(12) United States Patent
Kojima et al.

(10) Patent No.: US 6,251,915 B1
(45) Date of Patent: Jun. 26, 2001

(54) METHOD FOR PREVENTION OF PROSTATE CANCER

(75) Inventors: Koichi Kojima, Yokohama; Tomowo Kobayashi, Tokyo, both of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/590,107

(22) Filed: Jun. 8, 2000

Related U.S. Application Data

(60) Division of application No. 09/378,800, filed on Aug. 23, 1999, now Pat. No. 6,093,722, which is a continuation-in-part of application No. PCT/JP98/00767, filed on Feb. 26, 1998.

(30) Foreign Application Priority Data

Feb. 26, 1997 (JP) .................................... 9-42335

(51) Int. Cl.⁷ ............................ A61K 31/58; A61K 35/00
(52) U.S. Cl. ............................................ 514/284
(58) Field of Search ............................. 514/284

(56) References Cited

U.S. PATENT DOCUMENTS

| | | |
|---|---|---|
| 4,732,897 | 3/1988 | Cainelli et al. . |
| 5,300,294 | 4/1994 | Johnson . |
| 5,302,621 | 4/1994 | Kojima et al. . |
| 5,496,556 | 3/1996 | Johnson . |
| 5,637,310 | 6/1997 | Johhson . |

FOREIGN PATENT DOCUMENTS

| | | |
|---|---|---|
| 0 285 383 A2 | 10/1988 | (EP) . |
| 0 547 691 A1 | 6/1993 | (EP) . |
| 8-73492 | 3/1996 | (JP) . |
| WO 92/00010 | 1/1992 | (WO) . |

OTHER PUBLICATIONS

CA 117:49007 Preparation of 3-oxo . . . Inhibitors, Kojima et al. (1992).
Thompson et al, *The Prostate*, vol 33, pp 217–221 (1997).*
Brawley et al, *European Journal of Cancer.*, vol 36, pp 1312–1315 (2000).*

* cited by examiner

*Primary Examiner*—Robert W. Ramsuer
(74) *Attorney, Agent, or Firm*—Frishauf, Holtz, Goodman, Langer & Chick, P.C.

(57) ABSTRACT

A method for treatment or prevention of prostate cancer by administering an effective amount of a compound of the formula (I) or a pharmaceutically acceptable salt or ester thereof. In formula (I) (which follows), each of $R^1$ and $R^2$ is a hydrogen atom, a hydroxyl group, a protected hydroxyl group or a lower alkoxy group.

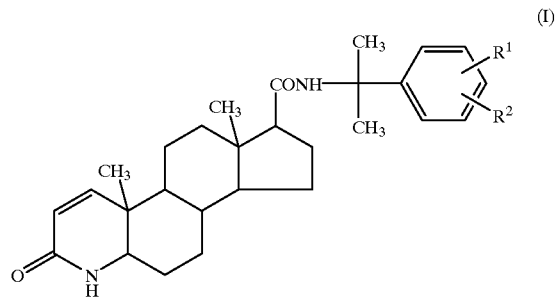

4 Claims, 1 Drawing Sheet

METHOD FOR PREVENTION OF PROSTATE CANCER

This application is a division of application Ser. No. 09/378,800 filed Aug. 23, 1999 (U.S. Pat. No. 6,043,722), which is a continuation-in-part of International Application PCT/JP98/00767 filed Feb. 26, 1998.

BACKGROUND OF THE INVENTION

Field of the Invention

The present invention relates to a novel composition for treatment or prevention of prostate cancer, use of a compound for producing a pharmaceutical preparation for treatment or prevention of prostate cancer, and a method of treating or preventing prostate cancer by administering an effective amount of the compound to warm-blooded animals.

BACKGROUND INFORMATION

Testosterone 5α reductase inhibitor is known as a therapeutic agent for benign prostatic hypertrophy that reduces prostate size by a mechanism of action that inhibits prostate cell growth caused by excessive male hormones (and mainly dihydrotestosterone). In addition, testosterone 5α reductase inhibitors such as Finasteride are sold as a therapeutic agent for benign prostatic hypertrophy in the United States of America and Europe. There are some testosterone 5α reductase inhibitors on which clinical studies are being conducted in order to develop them as therapeutic agents for prostate cancer.

The reductive effects on the prostate correspond to the potency of testosterone 5α reductase inhibitory activity. Different from benign prostatic hypertrophy, however, therapeutic effects on prostate cancer do not correspond to the potency of testosterone 5α reductase inhibitory activity alone, since a greater number of factors are involved with respect to proliferation of prostate cancer.

N-[1-methyl-1-(4-methoxyphenyl)ethyl]-3-oxo-4-aza-5α-androst-1-ene-17β-carboxamide is a compound disclosed in Japanese Patent Application (Kokai) No. Hei 8-73492 and Japanese Patent Publication (Kokoku) No. Hei 8-19151, and is a testosterone 5α reductase inhibitor.

SUMMARY OF THE INVENTION

The inventors of the present invention conducted an earnest research on the synthesis of derivatives having testosterone 5α reductase inhibitory activity and their pharmacological activity over many years. The inventors found that compounds like that mentioned above having a specific structure have an excellent prostate cancer therapeutic or preventive effect and accomplished the present invention.

The object of the present invention is to provide a composition for treatment or prevention of prostate cancer. In addition, another object of the present invention is to provide a use of the above-mentioned compound for the manufacture of a pharmaceutical for treatment or prevention of prostate cancer, and a therapeutic or preventive method for prostate cancer by administering an effective amount of the specified compounds) to warm-blooded animals.

The novel composition for treating or preventing prostate cancer of the present invention contains as its active ingredient a compound represented by the formula (I) below or pharmacologically acceptable salts thereof, preferably contains as its active ingredient N-[1-methyl-1-(4-methoxyphenyl)ethyl]-3-oxo-4-aza-5α-androst-1-ene-17β-carboxamide, and more preferably is taken orally.

In addition, the novel use of a compound represented by the formula (I) below or pharmacologically acceptable salts thereof to produce a pharmaceutical for treatment or prevention of prostate cancer, preferably the use of N-[1-methyl-1-(4-methoxyphenyl)ethyl]-3-oxo-4-aza-5α-androst-1-ene-17β-carboxamide for producing a pharmaceutical for treatment or prevention of prostate cancer, and more preferably it is taken orally.

The novel therapeutic or preventive method of the present invention is a therapeutic or preventive method for prostate cancer comprising the administration of an effective amount of a compound represented by the formula (I) below or pharmacologically acceptable salts thereof to warm-blooded animals, preferably a therapeutic or preventive method for prostate cancer comprising the administration of an effective amount of N-[1-methyl-1-(4-methoxyphenyl)ethyl]-3-oxo-4-aza-5α-androst-1-ene-17β-carboxamide to warm-blooded animals, and more preferably by taking it orally.

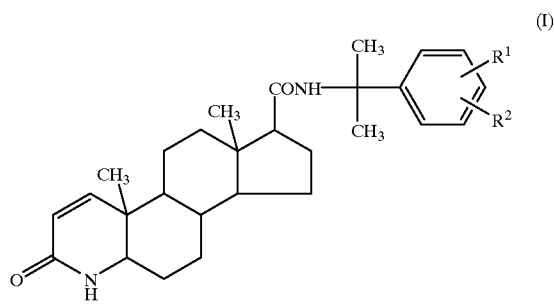

wherein $R^1$ and $R^2$ may be the same or different and represent a hydrogen atom, a hydroxyl group, a protected hydroxyl group, or a lower alkoxy group.

In the formula (I), the term "lower akoxy group" means a straight chain or branched chain alkoxy group having from 1 to 6 carbon atoms such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy, preferably a straight chain or branched chain alkoxy group having from 1 to 4 carbon atoms, more preferably a methoxy group.

The term "pharmacologically acceptable salts thereof" means the salts of the compound (I) of the present invention, which can be converted to salts thereof, examples of such salts preferably include alkali metal salts such as a sodium salt, a potassium salt and a lithium salt, alkaline earth metal salts such as a calcium salt and a magnesium salt, and metal salts such as an aluminum salt, an iron salt and a zinc salt.

Further, the compound (I) of the present invention, when it is allowed to stand in the atmosphere, may absorb some moisture, and it may, as a result, be a ssociated with absorption water or it may be converted to a corresponding hydrate. Such compounds are also included in the present invention.

The compound (I) of the present invention can be prepared according to the process shown below.

Process A

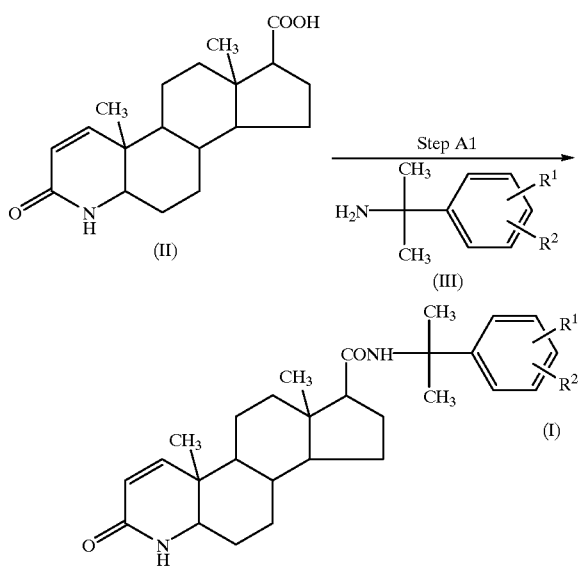

wherein R¹ and R² have the same meanings as defined above.

Process A is a method for preparing the desired compound (I) by condensing a carboxylic acid derivative (II) with an amine derivative (III).

Step A1 is to prepare the compound (I) by a reaction of compound (II) or a reactive derivative thereof with a compound (III). The reaction is carried out according to the conventional methods in peptide synthesis, for example an azide method, an active ester method, a mixed acid anhydride method or a condensation method.

In the above methods, the azide method is carried out as follows: the compound (II) or an ester thereof is reacted with hydrazine in an inert solvent (for example, dimethylformamide) at approximately room temperature to prepare an amino acid hydrazide. The amino acid hydrazide is reacted with a nitrous acid compound to afford an azide derivative, followed by the treatment of the azide derivative with an amine derivative (III).

The nitrous acid compound employable here may include, for example, alkali metal nitrites such as sodium nitrite or alkyl nitrites such as isoamyl nitrite.

The reaction is preferably carried out in an inert solvent, and the solvent employable here may include, for example, amides such as dimethylformamide and dimethylacetamide, sulfoxides such as dimethyl sulfoxide and pyrrolidones such as N-methylpyrrolidone. Two step reactions (preparation of azide and amide derivative (I)) are generally carried out in one reaction pot. The reaction temperature is −50° C. to 0° C. for the former reaction and −10° C. to 10° C. for the latter reaction, and the reaction time is 5 minutes to 1 hour for the former reaction and 10 hours to 5 days for the latter reaction.

The active ester method is carried out by a reaction of the compound (II) with an active esterification agent to give an active ester, followed by reaction of the active ester with an amine derivative (III).

Both reactions are preferably carried out in an inert solvent, and the solvent employable here may include, for example, halogenated hydrocarbons such as methylene chloride and chloroform, ethers such as diethylether and tetrahydrofuran, amides such as dimethylformamide and dimethylacetamide, and nitriles such as acetonitrile.

The active esterification agent employable here may include, for example, N-hydroxyl compounds such as N-hydroxysuccinimide, 1-hydroxybenzotriazole and N-hydroxy-5-norbornene-2,3- dicarboximide or disulfide compounds such as dipyridyldisulfide, and the active esterification reaction is preferably carried out in the presence of a condensation agent such as dicyclohexyl-carbodiimide, carbonyldiimidazole or triphenylphosphine.

The reaction temperature is −10° C. to 100° C. in the active esterification reaction and approximately room temperature in the reaction, of the active ester compound with the amine derivative (III) , and the reaction time is 30 minutes to 80 hours for both reactions.

In the reaction of the active ester with the amine, 4-dimethylaminopyridine may be added to the reaction system.

The mixed acid anhydride method is carried out by preparing a mixed acid anhydride of the compound (II) , followed by reaction of the mixed acid anhydride with an amine derivative.

The reaction for preparing the mixed acid anhydride derivative is accomplished by a reaction of the compound (II) with an agent for forming a mixed acid anhydride derivative (for example, lower ($C_1$–$C_4$) alkyl halogenated carbonic acids such as ethyl chlorocarbonate and isobutyl chlorocarbonate, lower alkanoyl halides such as pivaloyl chloride, lower alkyl or diaryl cyanophosphoric acids such as diethyl cyanophosphate and diphenyl cyanophosphate, or sulfonyl halides such as 2,4,6-triisopropylbenzenesulfonyl chloride, paratoluenesulfonyl chloride and methanesulfonyl chloride) in an inert solvent (for example, the halogenated hydrocarbons, amides and ethers described above). The reaction is preferably carried out in the presence of organic amines such as triethylamine and N-methyl morpholine, and the reaction temperature is −10° C. to 50° C. and the reaction time is 30 minutes to 20 hours.

The reaction of the mixed acid anhydride derivative with the amine derivative (III) is preferably carried out in an inert solvent (for example, the halogenated hydrocarbons, amides and ethers described above) in the presence of the organic amines. The reaction temperature is 0 ° C. to 80° C. and the time required for the reaction is 1 hour to 48 hours.

The reaction is carried out in the coexistence of the compound (II), the compound (III) and an agent for forming a mixed acid anhydride derivative without isolation of a mixed acid anhydride derivative.

The condensation method is carried out by a reaction of the compound (II) with the amine derivative (III) directly in the presence of a condensation agent such as dicyclohexyl-carbodiimide, carbonyldiimidazole or 2-chloro-1-methylpyridinium iodide/triethylamine. The present reaction is carried out in a similar manner to that described in the preparation of the active ester.

In the case where a protected hydroxyl group is present in $R^1$ and $R^2$ , the protecting group can be removed according to conventional methods.

The raw material compound (II) or the active ester thereof is known or is prepared according to known methods (for example, J. Med. Chem., 27, 1690 (1984); J. Med. Chem., 29, 2298 (1986))

Further, the compound (III) is known or is prepared according to known methods, for example:

Synthesis, 593 (1976);

J. Org. Chem., 36, 305 (1971);

Angew. Chem., 82, 138 (1970);

Synthesis, 24 (1978);

Synthetic Commun., 18, 777 (1988);

Synthetic Commun., 18, 783 (1988);

Organic Reaction, 3, 337 (1946);
Org. Synthesis, 51, 48 (1971);
Tetrahedron. 30, 2151 (1974); and
J. Org. Chem., 37, 183 (1972)], and, for example, a raw material compound of the present invention having a $H_2N-C(Me)(Me)-Ph(R^1)(R^2)$ moiety is prepared according to the method described in Synthesis, P. 24 (1978). The reaction scheme is shown below:

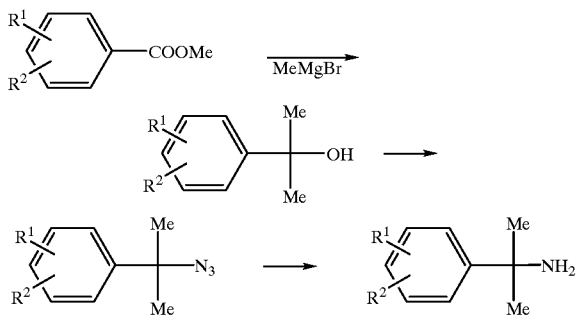

(wherein $R^1$ and $R^2$ have the same meanings as defined above, Me represents a methyl group and Ph represents a phenyl group), and comprises a Grignard reaction, an azidation reaction of hydroxyl group and a reduction reaction.

The "protecting group" of the term "protected hydroxyl group" means "conventional protecting group " or a "protecting group which can be cleaved in vivo by a biological method such as hydrolysis".

The "conventional protecting group" means a protecting group which can be cleaved by a chemical method such as hydrogenolysis, hydrolysis, electrolysis or photolysis.

Preferred examples of the "conventional protecting group" for the hydroxyl group include "lower aliphatic acyl groups" for example, lower alkylcarbonyl group such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl;, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl, carboxyl-substituted alkylcarbonyl group such as succinoyl, glutanoyl and adipoyl, halogen-substituted alkylcarbonyl group such as chloroacetyl, dichloroacetyl, trichloroacetyl and trifluoroacetyl, lower alkoxy-substituted alkylcarbonyl group such as methoxyacethyl, unsaturated alkylcarbonyl group such as (E)-2-methyl-2-buthenoyl; "aromatic acyl groups" for example, arylcarbonyl group such as benzoyl, α-naphthoyl and β-naphthoyl, halogenated arylcarbonyl group such as 2-bromobenzoyl and 4-chloro-benzoyl, lower alkyl-substituted arylcarbonyl group such as 2,4,6-trimethyl-benzoyl and 4-toluoyl, hydroxy-substituted arylcarbonyl group such as 3,5-dimethyl-4-hydroxybenzoyl and 3,5-di-t-butyl-4-hydroxybenzoyl, lower alkoxy-substituted arylcarbonyl group such as 4-anisoyl group, nitro-substituted arylcarbonyl group such as 4-nitrobenzoyl and 2-nitro-benzoyl, lower alkoxycarbonyl-substituted arylcarbonyl group such as 2-(methoxycarbonyl)benzoyl group; aryl-substituted arylcarbonyl group such as 4-phenylbenzoyl group; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2 and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups", for example, tri(lower alkyl)silyl groups such as trimethylsilyl, triethylsilyl, isopropyldimethylsilyl, t-butyldimethylsilyl, methyldiisopropylsilyl, methyl-di-t-butylsilyl and triisopropylsilyl and tri (lower alkyl) silyl group substituted with 1or 2 aryl groups such as diphenylmethylsilyl, diphenylbutylsilyl, diphenylisopropylsilyl and phenyldiisopropylsilyl; "alkoxymethyl groups", for example, lower alkoxymethyl groups such as methoxymethyl, 1,1-dimethyl-1-methoxymethyl, ethoxymethyl, propoxymethyl, isopropoxymethyl, butoxymethyl and tert-butoxymethyl, lower alkoxymethyl groups substituted with lower alkoxy such as 2-methoxyethoxymethyl and (halogeno lower alkoxy)methyl groups such as 2,2,2-trichloroethoxymethyl and bis(2-chloroethoxy)methyl; "substituted ethyl groups", for example, ethyl group substituted with lower alkoxy such as 1-ethoxyethyl and 1-(isopropoxy)ethyl and halogenated ethyl groups such as 2,2,2-trichloroethyl"; "aralkyl groups", for example, lower alkyl groups substituted with 1 to 3 aryl groups such as benzyl, α-naphthylmethyl, β-naphthylmethyl, diphenylmethyl, triphenylmethyl, α-naphthyldiphenylmethyl and 9-anthrylmethyl and lower alkyl groups each substituted with 1 to 3 aryl groups having an aryl substituted with a lower alkyl, halogeno (lower alkyl), lower alkoxy, nitro, halogen or cyano group such as 4-methylbenzyl, 2,4,6-trimtethylbenzyl, 3,4,5-trimethylbenzyl, 3,5-di(trifluoromethyl)benzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl; "lower alkoxycarbonyl groups" such as methoxycarbonyl, ethoxycarbonyl, tert-buthoxycarbonyl and isobuthoxycarbonyl,; "lower alkenyloxycarbonyl groups" such as vinyloxycarbonyl and allyloxycarbonyl; and "aralkyloxycarbonyl groups", for example, aryl substituted with 1 or 2 lower alkoxy or nitro group such as 4-methoxybenzyloxycarbonyl, 3,4-dimethoxylbenzyloxycarbonyl, 2-nitrobenzyloxycarbonyl and 4-nitrobenzyloxycarbonyl.

The "protecting group which can be cleaved in vivo by a biological method such as hydrolysis" means a protecting group which is cleaved in vivo by a biological method such as hydrolysis and forms a free acid or salt thereof. It can be determined whether an ester is such a derivative by administering it to an experimental animal, such as a rat or mouse, by intravenous injection, examining the body fluid of the animal after administration and detecting an original compound or a pharmaceutically acceptable salt thereof.

Preferred examples of the "protecting group which can be cleaved in vivo by a biological method such as hydrolysis" for the hydroxyl group include 1-(acyloxy) "lower alkyl groups", for example, 1-("lower aliphatic acyl"oxy) "lower alkyl groups" such as formyloxymethyl, acetoxymethyl, dimethylaminoacetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxypropyl, 1-isovaleryloxypropyl, 1-hexanoyloxypropyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl, 1-("cycloalkyl"carbonyloxy)"lower alkyl groups" such as cyclopentylcarbonyloxymethyl, cyclohexylcarbonyloxymethyl, 1-cyclopentylcarbonyloxyethyl, 1-cyclohexylcarbonyloxethyl, 1-cyclopentylcarbonyloxypropyl, 1-cyclohexylcarbonyloxypropyl, 1-cylopentylcarbonyloxybutyl and 1-cyclohexylcarbonyloxybutyl, and 1-("aromatic acyl"oxy) "lower alkyl groups" such as benzoyloxymethyl; (lower alkoxycarbonyloxy) alkyl groups such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1(ethoxycarbonyloxy)ethyl, 1-(propoxycarbonyloxy)ethyl, 1-(isopropoxycarbonyloxy)ethyl, 1-(butoxycarbonyloxy)ethyl, 1-isobutoxycarbonyloxy)ethyl, 1-(tert-butoxycarbonyloxy)ethyl, 1-(pentyloxycarbonyloxy)ethyl, 1-(hexyloxycarbonyloxy)ethyl, 1-(cyclopentyloxycarbonyloxy ethyl, 1-(cyclopentyloxycarbonyloxy)propyl, 1-(cyclohexyloxycarbonyloxy) propyl, 1-(cyclopentyloxycarbonyloxy)butyl 1-(cyclohexyloxycarbonyloxy)butyl, 1-(cyclohexyloxycarbonyloxy) ethyl, 1-(ethoxycarbonyloxy)propyl, 2-(methoxycarbonyloxy)ethyl, 2-(ethoxycarbonyloxy) ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(pentyloxycarbonyloxy)ethyl, 2-(hexyloxycarbonyloxy)ethyl, 1-methoxycarbonyloxy)propyl, 1-(ethoxycarbonyloxy)propyl, 1-(propoxycarbonyloxy)propyl, 1-(isopropoxycarbonyloxy)propyl, 1-butoxycarbonyloxy)propyl, 1-(isobutoxycarbonyloxy) propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl and 1-(ethoxycarbonyloxy)hexyl; and oxodioxolenylmethyl groups such as (5-phenyl-2-oxo-1,3-dioxolen-4-yl)methyl, [5-(4-methoxyphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl) methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl: "phthalidyl groups" such as phthalidyl, dimethylphthalidyl and dimethoxyphthalidyl: the above-described "lower aliphatic acyl groups": the above-described "aromatic acyl groups": "half ester salt residue of succinic acid": "phosphate salt residue": "ester forming residues such as with amino acids": carbamoyl groups: carbamoyl group substituted with 1 or 2 lower alkyl groups: and "1-(acyloxy)alkyloxycarbonyl groups" such as pivaloyloxymethyloxycarbonyl, of which the "carbonyloxy- alkyl groups" are preferred. Pharmacologically acceptable esters are preferred.

DESCRIPTION OF THE DRAWING

The FIGURE is a graph which shows an antitumor effect against a human prostate cancer in Example 1.

In the FIGURE, the vertical axis is the relative ratio of tumor volume (expressed in logarithm). The horizontal axis is the Number of days after initial administration. The cross dots are the Control group; the black dots are the Finasteride administration group; and the circlet dots are the Compound 1 administration group.

Figure 1:
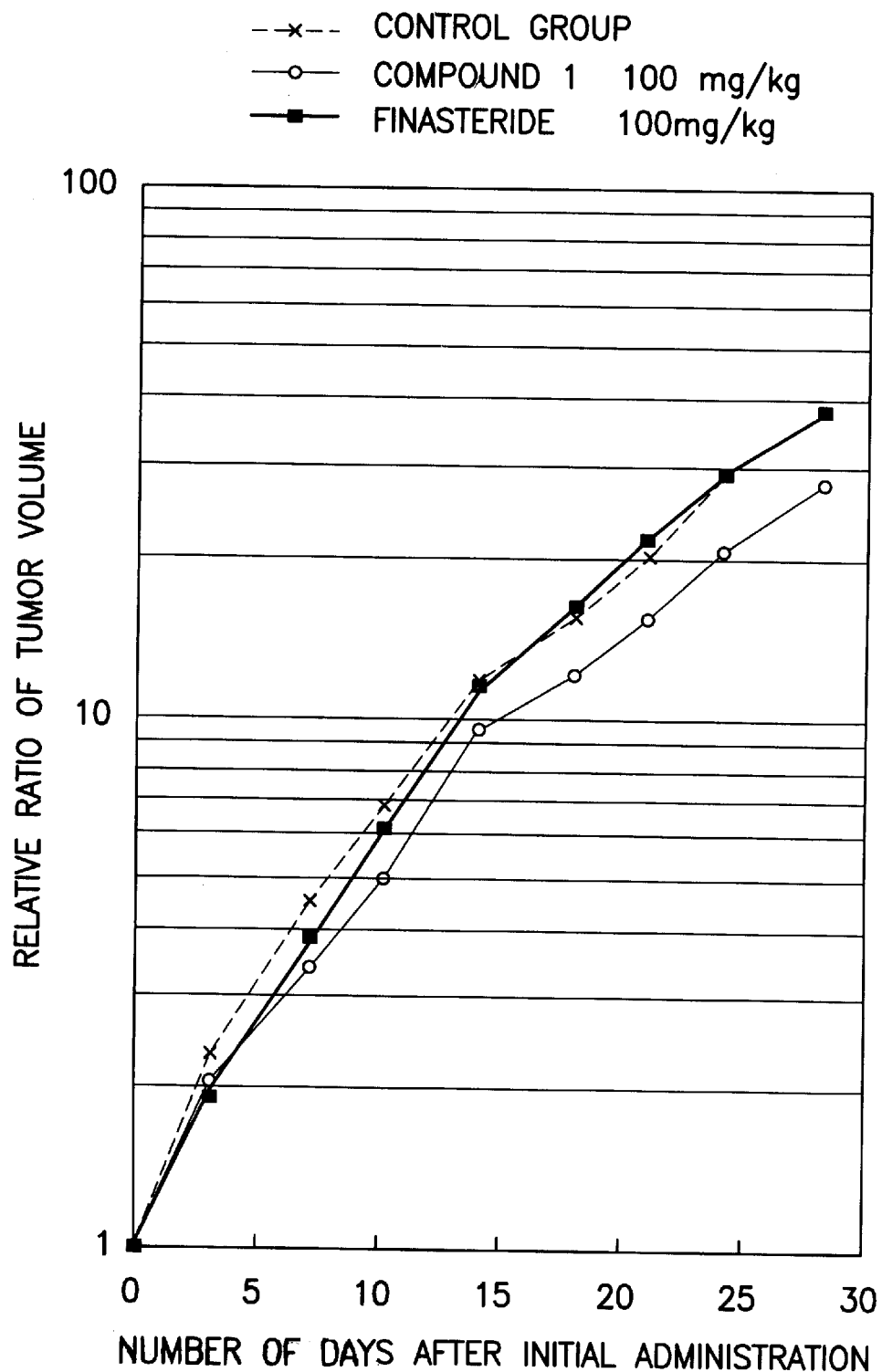

Compound 1 is 1N-[1-methyl-1-(4-methoxyphenyl)ethyl]-3-oxo-4-aza-5α-androst-1-ene-17β-carboxamide.

In the following, the present invention will be described in further detail with reference to Examples and Reference Example 1, but the scope of the present invention is not limited thereto.

EXAMPLE 1

Antitumor Activity Test 1

A solid tumor, which was reliably taken beneath the skin was obtained by subculturing subcutaneously human prostate cancer strain LNCaP of a cultured cell system purchased from the American Type Culture Collection (ATCC) five to six times in male and female nude mice. This human prostate cancer strain was used in the Lest. A solid cancer fragment of this strain 3 mm square was transplanted beneath the skin of the axillary region of BALB/cA Jcl-nu nude mice (Nippon Clea, males, 8 weeks old). Mice in which the tumor was reliably taken about 20 days later were randomly assigned to groups of 8–10 animals each. N-[1-methyl-1-(4-methoxyphenyl)ethyl]-3-oxo-4-aza-5α-androst-1-ene-17β-carboxamide (compound 1, 100 mg/kg) or Finasteride (100 mg/kg) were orally administered to the mice at the rate of 0.1 ml/10 g of body weight once a day in the morning for 28 consecutive days. Tumor diameter was measured twice a week, and tumor volume V (V=ab$^2$/2) was calculated from the major axis (a) and minor axis (b). The relative volume ratio for each mouse was represented as Vn/Vo. The tumor growth inhibition rate (%) was determined from the relative volume ratio for each mouse.

Tumor growth inhibition rate (%)=(1Vn/Vo)×100

Vn: Tumor volume on nth day

Vo: Tumor volume on first day of administration

Results

Relative volume ratio data is shown in the FIGURE.

Finasteride is sold in the United States of America and Europe as a drug for the treatment of benign prostatic hypertrophy, and clinical studies for its use as a drug for the treatment of prostate cancer are currently being conducted.

The FIGURE shows that Finasteride does not exhibit any tumor growth inhibitory activity whatsoever, but the compound 1, however, exhibits tumor growth inhibitory activity of which the maximum tumor inhibition rate for 28 days was 30%. Accordingly, the compound 1 is useful as a therapeutic agent for prostate cancer.

EXAMPLE 2

Antitumor Activity Test 2

Male nude mice (age 4–5 weeks) without thymus gland were used in the test. The nude mice were bred in an aseptic condition.

Human prostate cancer LNCaP cells were purchased from the American Type Culture Collection (ATCC). LNCaP cells ($5\times10^6$) were subcutaneously transplanted to the nude mice to form a solid tumor and then used in the test.

The lower abdomens of the nude mice were incised about 2 cm under anesthesia to expose the prostate. The prostate membrane was carefully opened, and a LNCaP tumor fragment was inserted inside. The opening in the prostate membrane was closed with absorbable suture. The prostate was returned in the abdominal cavity, and the incision in the lower abdomen was sutured with absorbable suture. These mice were randomly assigned to groups of 20 animals each. These groups were designated as compound 1 group to which compound 1 (20 mg/kg) was administered, Finasteride group to which Finasteride (20 mg/kg) was administered and non-dosed control group.

The transplanted tumor was confirmed to be taken into the mouse when the tumor grew until it could be measured from outside the mouse body, and then administration of compound (1) and Finasteride was started. The compound 1 and Finasteride were orally administered daily at the dose levels described above. The volume of the transplanted tumor was calculated according to the formula shown in Example 1. In addition, the mice were immediately necropsied when they died due to the cancer and the tumor was weighed. The presence of metastasis was also confirmed at the same time. Tissue section of metastasis was prepared by imbedding in paraffin after fixing with 10% formalin. The tissue sections were stained with hematoxylin and eosin followed by examination of the metastasis.

Student's t-test was performed on the transplanted tumor weights for all groups. In addition, Fisher's test was performed on cases of metastasis in each of the groups. The Mann-Whitney U-test and Student's t-test were performed on the two groups used for comparison with respect to life-extending effects. The chi squared ($X^2$) test according to Pearson was performed on survival rate on day 63 after tumor transplantation in particular. The hazard rate of less than 5% was regarded as significant for these tests.

Results

TABLE 1

| Experimental Group | Survival Rate (%) |
| --- | --- |
| Control group | 0 |
| Compound 1 | 56 |
| Finasteride | 22 |

As is clear from Table 1, the compound 1 group exhibited a much better survival rate in comparison with the Finasteride group.

Reference Example 1

N-[1-Methyl-1-(4-methoxyphenyl)ethyl]-3-oxo-4-aza-5α-androst-1-ene-17β-carboxamide 1.0 g of 3-oxo-4-aza-5α-androst-1-ene-17β-carboxylic acid, 1.6 g of triphenylphosphine and 1.4 g of 2,2'-dipyridyldisulfide were successively added to 30 ml of dry toluene and the mixture was stirred at room temperature overnight. The reaction mixture as such was subjected to column chromatography on 35 g of silica gel and was eluted with acetone/methylene chloride (1:9 to 1:1) to obtain 1.11 g of 2-pyiridylthio ester derivative.

5.0 g of 2-pyiridylthio ester derivative synthesized in a similar manner to that described above and 5.0 g of 1-(4-methoxyphenyl)-1-methylethylamine were added successively to 30 ml of dry methylene chloride and the mixture was stirred at room temperature for 3 days. The reaction mixture was diluted with 100 ml of methylene chloride, washed with 1N hydrochloric acid, water, aqueous sodium hydrogencarbonate and a saturated saline solution successively. The methylene chloride layer was dried over magnesium sulfate and then concentrated under reduced pressure. The residue was subjected to column chromatography on 15 g of silica gel and was eluted with acetone/methylene chloride (1:9 to 1:1) to obtain 5.2 g of the title compound.

NMR spectra (CDCL$_3$) δ ppm: 0.68 (3H, s), 0.98 (3H, s), 0.90–2.20 (16H, m), 1.70 (3H, s), 1.72 (3H, s), 3.35 (1H, t, J=9 Hz), 3.80 (3H, s), 5.48 (1H, br.), 5.76 (1H, br.), 5.83 (1H, d, J=10 Hz), 6.82 (1H, d, J=10 Hz), 6.88 (2H, d, J=9 Hz), 7.32 (2H, d, J=9 Hz)

IR spectra $v_{max}$cm$^{-1}$ (KBr): 2969, 2938, 1672, 1599, 1514, 1455, 1248, 1181, 1035, 825.

The compound (I) of the present invention has excellent antitumor activity and it is weak in toxicity. Thus, it is useful as a composition for treatment or prevention of prostate cancer.

The compound (I) or the pharmacologically acceptable salts thereof of the present invention is used as a composition for treatment or prevention of prostate cancer. The compound (I) itself or mixtures of compound (I) with appropriately pharmacologically acceptable excipients, diluents and the like can be orally administered as tablets, capsules, granules, powders or syrups.

These pharmaceutical preparations are prepared by standard techniques that are well known to those skilled in the art using additives. The additives are excipients (for example, organic excipients such as sugar derivatives, e.g. lactose, sucrose, glucose, mannitol and sorbitol; starch derivatives such as corn starch, potato starch, α-starch, dextrin and carboxymethyl starch; cellulose derivatives such as crystalline cellulose, low substituted hydroxyproyl cellulose, hydroxypropylmethyl cellulose, carboxymethyl cellulose, calcium carboxymethyl cellulose and internally bridged sodium carboxymethyl cellulose; gum Arabic; dextran; and Pullulan; and inorganic excipients such as silicate derivatives, e.g. light silicic acid anhydride, synthetic aluminum silicate and magnesium meta-silicic acid aluminate; phosphates, e.g. calcium phosphate; carbonates, e.g. calcium carbonate; and sulfates, e.g. calcium sulfate); lubricants (for example, stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; sodium salts of aliphatic acid; laurylsulfates such as sodium laurylsulfate and magnesium laurylsulfate; silicic acids such as silicic acid anhydride and silicic acid hydrate; and the above-mentioned starch derivatives); binders (for example, polyvinyl pyrrolidone, Macrogol and the same compounds as described in the above excipients); disintegrants (for example, the same compounds as described in the above excipients; and chemically modified starches and celluloses such as sodium Crosscarmelose, sodium carboxymethyl starch and bridged polyvinyl pyrrolidone); stabilizers (for example, para-oxybenzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid); corrigents (for example, sweetening agents, acidifiers and aroma chemicals conventionally used); and diluents.

The dose varies depending on the condition and age of the patient, e.g. a human. For example, it is desirable to administer 0.001 mg/kg body weight (preferably 0.01 mg/kg body weight) as a lower limit and 20 mg/kg body weight (preferably 1 mg/kg body weight) as an upper limit once to several times a day depending on the symptoms.

Preparation examples are shown as follows. However, the scope of the invention is not limited to these examples.

Preparation Example 1

| Capsules | |
| --- | --- |
| Compound of Reference Example 1 | 20.0 mg |
| Lactose | 158.7 |
| Corn starch | 70.0 |
| Magnesium stearate | 1.3 |
| | 250 mg |

Powders described above were mixed and sieved through 60 mesh sieve and then the resulting powders were encapsulated in a No. 3 gelatin capsule of 250 mg to give a capsule.

Preparation Example 2

| Tablets | |
| --- | --- |
| Compound of Reference Example 1 | 20.0 mg |
| Lactose | 154.0 |
| Corn starch | 25.0 |
| Magnesium stearate | 200 mg |

Powders described above were mixed and formed into a tablet using a tablet making machine to obtain a tablet of 200 mg.

The tablet may be coated with sugar, if desired.

We claim:

1. A method for the prevention of prostate cancer, which comprises administering to a male warm-blooded animal in need thereof an anti-prostate cancer effective amount of an anti-cancer agent comprising N-[1-methyl-1-(4-methoxyphenyl)ethyl]-3-oxo-4-aza-5α-androst-1-ene-17β-carboxamide or a pharmacologically acceptable salt or ester thereof.

2. The method according to claim 1, wherein said anti-prostate cancer agent is administered orally.

3. The method according to claim 1, wherein said anti-prostate cancer agent is administered to a human.

4. The method according to claim 2, wherein the warm-blooded animal is a human.

* * * * *